US011786271B2

(12) United States Patent
Govari et al.

(10) Patent No.: US 11,786,271 B2
(45) Date of Patent: Oct. 17, 2023

(54) TROCAR WITH MODULAR OBTURATOR HEAD

(71) Applicant: BIOSENSE WEBSTER (ISRAEL) LTD., Yokneam (IL)

(72) Inventors: Assaf Govari, Haifa (IL); Yehuda Algawi, Binyamina (IL); Ilya Sitnitsky, Nahariya (IL); Stanislav Katzir, Hadera (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 655 days.

(21) Appl. No.: 16/729,433

(22) Filed: Dec. 29, 2019

(65) Prior Publication Data

US 2021/0196314 A1 Jul. 1, 2021

(51) Int. Cl.
| A61B 17/34 | (2006.01) |
| A61B 1/05 | (2006.01) |
| A61B 5/06 | (2006.01) |
| A61B 1/018 | (2006.01) |
| A61B 17/00 | (2006.01) |

(52) U.S. Cl.
CPC .......... *A61B 17/3423* (2013.01); *A61B 1/018* (2013.01); *A61B 1/05* (2013.01); *A61B 5/062* (2013.01); *A61B 5/066* (2013.01); *A61B 17/3496* (2013.01); *A61B 2017/00199* (2013.01)

(58) Field of Classification Search
CPC . A61B 17/3423; A61B 17/3496; A61B 1/018; A61B 1/05; A61B 5/062; A61B 5/068
See application file for complete search history.

(56) References Cited

U.S. PATENT DOCUMENTS

| 5,350,393 A * | 9/1994 | Yoon .................. A61B 17/3496 604/164.12 |
| 5,391,199 A | 2/1995 | Ben-Haim |
| 5,405,328 A * | 4/1995 | Vidal ................. A61B 17/3417 604/274 |
| 5,807,338 A | 9/1998 | Smith et al. |
| 5,817,061 A | 10/1998 | Goodwin et al. |
| 6,106,539 A | 8/2000 | Fortier |
| 6,221,007 B1 | 4/2001 | Green |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |

(Continued)

FOREIGN PATENT DOCUMENTS

WO WO9605768 2/1996

OTHER PUBLICATIONS

International Search Report and Written Opinion dated Apr. 1, 2021, for International Application No. PCT/IB2020/061562, 14 pages.

*Primary Examiner* — Anh Tuan T Nguyen
*Assistant Examiner* — Rynae E Boler
(74) *Attorney, Agent, or Firm* — Frost Brown Todd LLP

(57) ABSTRACT

A trocar for insertion into an organ of a patient includes a cannula, an obturator body, and two or more interchangeable obturator heads. The cannula has a longitudinal axis. The obturator body is configured to be inserted into the cannula. The two or more interchangeable obturator heads are each configured to be detachably fitted at a distal end of the obturator body.

17 Claims, 3 Drawing Sheets

(56) References Cited

U.S. PATENT DOCUMENTS

| | | |
|---|---|---|
| 6,690,963 B2 | 2/2004 | Ben-Haim et al. |
| 7,044,937 B1 | 5/2006 | Kirwan et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0230217 A1 | 11/2004 | O'Heeron |
| 2006/0004286 A1* | 1/2006 | Chang .................... A61B 90/16 606/198 |
| 2008/0249467 A1* | 10/2008 | Burnett .................. A61B 1/313 604/117 |
| 2010/0100045 A1 | 4/2010 | Pravongviengkham et al. |
| 2011/0160535 A1* | 6/2011 | Bayer ................ A61B 1/00154 600/114 |
| 2013/0282041 A1 | 10/2013 | Gunday et al. |
| 2014/0180063 A1* | 6/2014 | Zhao ........................ G06T 7/75 600/424 |
| 2015/0272617 A1* | 10/2015 | MacDonald ....... A61B 1/00183 600/110 |
| 2016/0045224 A1* | 2/2016 | Hendershot, III . A61B 17/3417 604/26 |
| 2016/0128722 A1 | 5/2016 | Mark et al. |
| 2018/0161024 A1* | 6/2018 | Davis .................. A61B 17/3421 |
| 2019/0167299 A1 | 6/2019 | Davis et al. |
| 2021/0196313 A1 | 7/2021 | Govari et al. |

\* cited by examiner

TROCAR WITH MODULAR OBTURATOR HEAD

CROSS-REFERENCE TO RELATED APPLICATIONS

This application is related to a U.S. Patent Application entitled "Navigated Trocar with Internal Camera," Ser. No. 16/729,432, filed on Dec. 29, 2019, published as U.S. Pub. No. 2021/0196313 on Jul. 1, 2021, whose disclosure is incorporated herein by reference.

FIELD OF THE INVENTION

The present invention relates generally to invasive medical tools, and particularly to invasive medical tools incorporating a camera.

BACKGROUND OF THE INVENTION

Techniques for image-guided probing of an organ of a patient were previously proposed in the patent literature. For example, U.S. Patent Application Publication 2011/0160535, now abandoned, describes a disposable access port for use in endoscopic procedures, including laparoscopic procedures. The access port includes a cannula with an embedded external camera in communication with an external control box. The camera can be fixedly or adjustably mounted on the port. An external camera may also be mounted on a trocar used with the access port. The trocar may include irrigation and suction channels to facilitate a clear view of the anatomical site.

As another example, U.S. Patent Application Publication 2013/0282041, issued as U.S. Pat. No. 10,166,039 on Jan. 1, 2019, describes a viewing trocar assembly including a tubular body having a proximal end and a distal end, and an opening provided at the distal end, and at least one external imaging device positioned on an outer wall of the distal end of the tubular body, wherein the at least one imaging, device is adjacent to the outer wall of the distal end of the tubular body when in an inactivated position, and wherein the at least one imaging device is extended further away from the outer wall of the distal end of the tubular body when in an activated position than when in the inactivated position.

Different trocars were previously proposed in the patent literature. For example, U.S. Pat. No. 5,807,338 describes a modular trocar system which includes an obturator assembly, and a cannula assembly defining a longitudinal passageway therethrough configured and dimensioned to slidably receive the obturator assembly. A method of assembly is also provided.

As another example, U.S. Pat. No. 5,405,328 describes a kit assembly for use to construct a desired trocar obturator used during a surgical procedure. The kit includes a proximal portion of the obturator and a plurality of different distal end portions. The proximal portion may be releasably attached to a distal portion by virtue of a detent mechanism. Reuse of the proximal portion affords potential cost savings. The plurality of distal end portions affords the surgeon a choice between different trocar tips so that the trocar may be customized for a particularly surgical procedure.

SUMMARY OF THE INVENTION

An embodiment of the present invention provides a trocar for insertion into an organ of a patient, the trocar including a cannula, a channel inside the cannula, and a camera. The cannula has a longitudinal axis, and the channel inside the cannula is fitted parallel to the longitudinal axis. The camera is disposed at a distal end of the channel and is configured to provide images in a direction of a distal opening of the cannula.

In some embodiments, the camera is tilted relative to the longitudinal axis, so as to have a viewing direction that captures a distal opening of the cannula.

In some embodiments, the trocar further includes a position sensor, which is disposed at a distal end of the channel without obstructing a field of view of the camera, and is configured to generate signals indicative of a position of the distal end in the organ.

In an embodiment, the position sensor is a magnetic position sensor.

There is additionally provided, in accordance with another embodiment of the present invention, a system including a trocar and a processor. The trocar is configured for insertion into an organ of a patient and includes a cannula, a channel inside the cannula, a camera, and a position sensor. The cannula has a longitudinal axis, and the channel inside the cannula is fitted parallel to the longitudinal axis. The camera is disposed at a distal end of the channel and is configured to provide images in a direction of a distal opening of the cannula. The position sensor is disposed at a distal end of the channel without obstructing a field of view of the camera, and is configured to generate signals indicative of a position of the distal end in the organ. The processor is configured to, using the signals generated by the position sensor, estimate the position of the distal end of the trocar in the organ.

In some embodiments, the processor is further configured to, based on the estimated position, register an image acquired by the camera with a reference medical image, and present the image acquired by the camera and the reference medical image, registered with one another, to a user.

There is further provided, in accordance with another embodiment of the present invention, a method including inserting a trocar into an organ of a patient, the trocar including a cannula, a channel inside the cannula, a camera, and a position sensor. The cannula has a longitudinal axis, and the channel inside the cannula is fitted parallel to the longitudinal axis. The camera is disposed at a distal end of the channel and is configured to provide images in a direction of a distal opening of the cannula. The position sensor is disposed at a distal end of the channel without obstructing a field of view of the camera, and is configured to generate signals indicative of a position of the distal end in the organ. Using on the generated signals, the position of the distal end of the trocar in the organ is estimated.

In some embodiments, the method further includes, based on the estimated position, registering an image acquired by the camera with a reference medical image. The image acquired by the camera and the reference medical image are presented Another embodiment of the present invention provides a trocar for insertion into an organ of a patient, the trocar including a cannula, an obturator body, and two or more interchangeable obturator heads. The cannula has a longitudinal axis. The obturator body is configured to be inserted into the cannula. The two or more interchangeable obturator heads are each configured to be detachably fitted at a distal end of the obturator body.

In some embodiments, the obturator heads have different respective geometries for penetrating different respective tissue types.

In some embodiments, the interchangeable obturator heads are configured for use in an invasive brain procedure.

In an embodiment, the trocar further includes a channel inside the cannula, a camera, and a position sensor. The channel inside the cannula is fitted parallel to the longitudinal axis. The camera is disposed at a distal end of the channel and is configured to provide images in a direction of a distal opening of the cannula. The position sensor is disposed at a distal end of the channel without obstructing a field of view of the camera, and is configured to generate signals indicative of a position of the distal end in the organ.

In another embodiment, the camera is tilted to have a center viewing direction of the camera point at a center of the distal opening of the cannula. In yet another embodiment, the position sensor is a magnetic position sensor.

In some embodiments, the obturator body includes a depression to conform with a channel inside the cannula when the obturator body is inserted into the cannula.

In some embodiments, the interchangeable obturator heads include each a depression to conform with a channel inside the cannula when the obturator is inserted into the cannula.

There is additionally provided, in accordance with another embodiment of the present invention, a method including selecting an obturator head from among two or more interchangeable obturator heads. The selected obturator head is detachably fitted at a distal end of an obturator body, to form an obturator. A trocar is assembled by fitting the obturator in a cannula. The trocar is inserted into an organ of a patient, so as to perform a medical procedure on the patient.

In some embodiments, the method further includes acquiring images in a direction of a distal opening of the cannula, by a camera disposed at a distal end of the cannula. Using a position sensor disposed at a distal end of the channel, without obstructing a field of view of the camera, signals indicative of a position of the distal end in the organ are generated. Using on the generated signals, the position of the distal end of the trocar in the organ is estimated.

In some embodiments, the method further includes, based on the estimated position, registering an image acquired by the camera with a reference medical image. The image acquired by the camera and the reference medical image are presented, registered with one another, to a user.

The present invention will be more fully understood from the following detailed description of the embodiments thereof, taken together with the drawings in which:

DETAILED DESCRIPTION OF EMBODIMENTS

Overview

Figure 1:
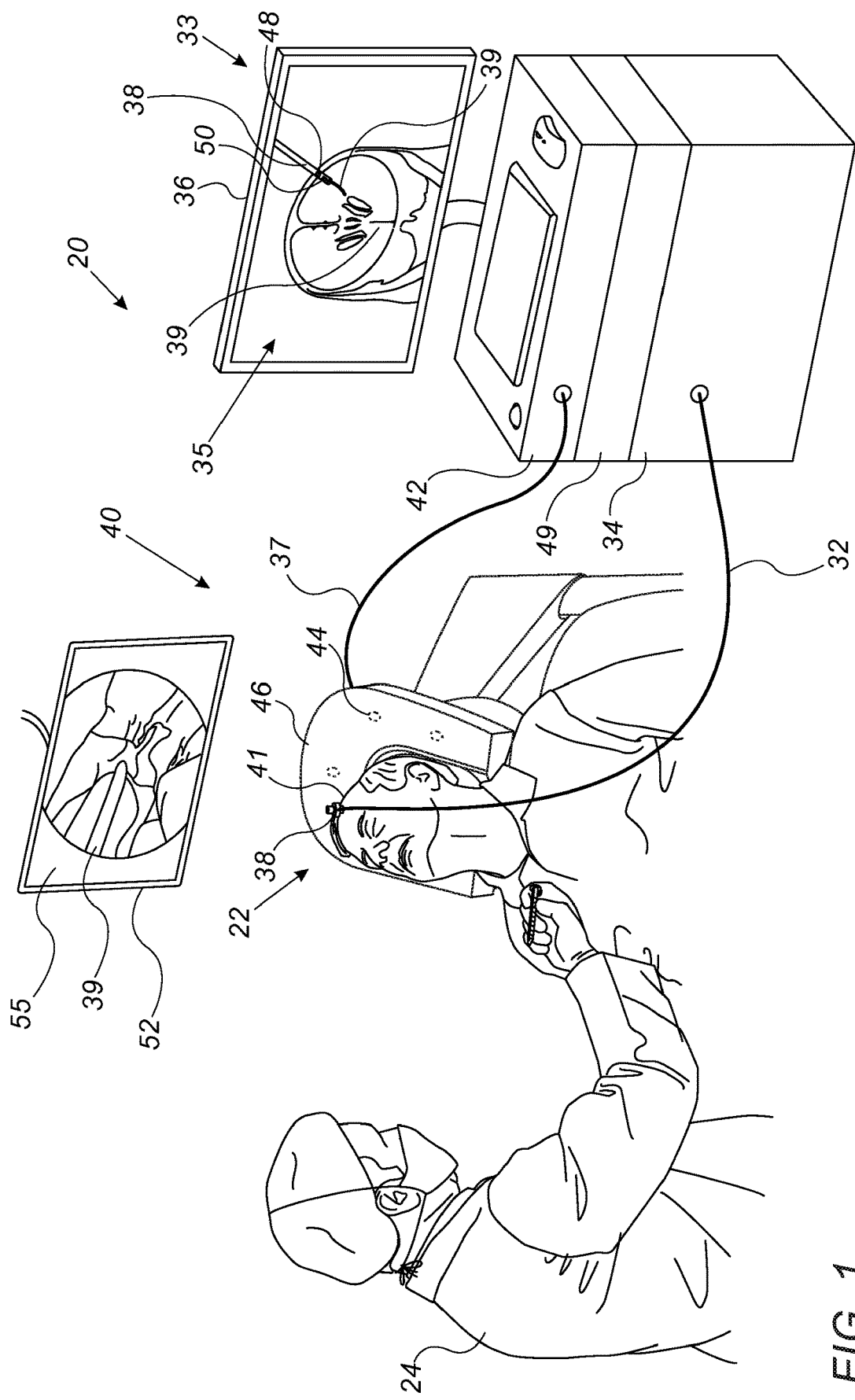
FIG. 1 is a schematic, pictorial illustration of a brain procedure using a surgical apparatus comprising a trocar comprising a camera and a position sensor, in accordance with an embodiment of the present invention.

In some invasive procedures, to insert a medical probe or other tool into the body of a patient, a trocar, which serves as a penetrating portal, is first placed in an entry location. In addition to being a portal for the probe, the trocar, which comprises a cannula, is used for irrigation and to drain bodily fluids, as well as other fluids. Typically, an obturator is first inserted via the cannula, so that the obturator can penetrate the body and create access for the probe.

Such invasive medical procedures typically require the use of dedicated imaging to guide the medical probe to and/or in an organ, such as a brain; for example, using an X-ray system and/or a camera fitted to the probe. In some cases, for example, brain procedures may require navigating a distal end of a probe inserted into the brain via a hole made in the skull. The treating probe has to be advanced via the trocar and be guided to treat the target brain tissue, for example infected or bleeding brain tissue.

Treating probes, however, are limited in space, while often visual guidance of the probe is required regardless of any other probe navigation techniques. Moreover, the trocar itself is conventionally inserted "blind," so that a physician performing the insertion cannot know exactly where the trocar distal end is located. The physician also cannot see tissue that the trocar is contacting.

Embodiments of the present invention that are described hereinafter provide a trocar that has a camera to view target tissue and/or a treating probe fitted internally to a wall of the cannula. In some embodiments, a position sensor is also fitted internally to a wall of the cannula. Sensor wiring, providing location data from the sensor, is passed from the sensor with the camera wiring to a processor that provides the physician with location data for the trocar distal end, for example, to register captured images from the camera with a reference medical image (e.g., an MRI image).

The disclosed internal camera and position sensor within the cannula (e.g., a magnetic position sensor operated with a position-tracking system) therefore enables the physician to see tissue being penetrated by the trocar, and the sensor allows the trocar distal end to be tracked. Subsequently, the camera may be used in visual guidance of a treating probe.

By optimizing visual image acquisition using an internal camera of a trocar, the disclosed technique may enable improved quality of minimally invasive medical procedures.

In general, trocars are relatively expensive, since they typically may also be precision instruments and must be capable of sterilization (by autoclaving or another method). There are many different types of trocars, depending on the tasks they are designed to perform. For example, a trocar with an obturator for penetrating muscle or bone may have a very sharp obturator head, whereas a trocar for penetrating brain tissue will have a smooth obturator head, in order to open access into brain as "gently" as possible. To form each of these different trocars with a camera and location sensor, as described above, would involve considerable expense.

In some embodiments of the present invention a modular trocar is provided, wherein the obturator head of the trocar may be selected by the physician according to the required obturator task. The obturator heads are sterilizable, and may be reused. The proximal end, which includes a camera and location sensor, is a low-cost disposable item, though it can be used multiple times during the same procedure by replacing obturator heads, as described below.

System Description

FIG. 1 is a schematic, pictorial illustration of a brain procedure using a surgical apparatus 28 comprising a trocar comprising a camera 50 and a position sensor 48, in accordance with an embodiment of the present invention. In some embodiments, a brain diagnostics and treatment system 20, which comprises surgical apparatus 28, is configured to carry out a brain procedure, such as treating an infection in brain tissue of a patient 22. In the shown embodiment, trocar 38 is used to penetrate the skull so that a physician 24 can insert a probe 39 into a head 41 of patient 22 (insertion not shown) to access brain tissue. Subsequently, probe 39 may be operated using the trocar-attached camera 50. Typically, treating probe 39 may be further operated by a second physician (not shown).

In the shown embodiment, a cable 32 enters a proximal end of trocar 38 and is electrically coupled on its distal end to camera 50 and position sensor 48.

System 20 comprises a magnetic position-tracking system, which is configured to track a position of sensor 48 in the brain. The magnetic position-tracking system comprises a location pad 40, which comprises field generators 44 fixed on a frame 46. In the exemplary configuration shown in FIG. 1, pad 40 comprises five field generators 44, but may alternatively comprise any other suitable number of generators 44. Pad 40 further comprises a pillow (not shown) placed under head 41 of patient 22, such that generators 44 are located at fixed, known positions external to head 41. The position sensor generates position signals in response to sensing external magnetic fields generated by field generators 44, thereby enabling a processor 34 to estimate the position of sensor 50 and therefore a position of a distal edge of trocar 38 inside the head of patient 22.

This technique of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1; issued as U.S. Pat. No. 6,690,963 on Feb. 10, 2004, 2003/0120150 A1; issued as U.S. Pat. No. 7,729,742 on Jun. 1, 2010, and 2004/0068178 A1; now abandoned, which prior applications are hereby incorporated by reference in their entirety herein into this application as if set forth in full.

In some embodiments, system 20 comprises a console 33, which comprises a memory 49, and a driver circuit 42 configured to drive field generators 44, via a cable 37, with suitable signals so as to generate magnetic fields in a predefined working volume in space around head 41.

Console 33 may further include additional control elements to assist physician 24 to perform the procedure, such as command buttons to capture an image from camera 50 and, using a position obtained by the magnetic position-tracking system, to register it with a reference medical image.

Processor 34 is typically a general-purpose computer, with suitable front end and interface circuits for receiving images from camera 50 and signals from position sensor 48 via cable 32, and for controlling other components of system 20 described herein.

In some embodiments, processor 34 is configured to register an image produced by camera 50 with a medical image, such as an MRI image. Processor 34 may further register the position of the distal end that is estimated using position sensor 48. Processor 34 is able to register a camera 50 image by estimating a position of a distal edge of trocar 38 using position sensor 48. Processor 34 is configured to register the camera image and the reference medical image in the coordinate system of the magnetic position-tracking system and/or in a coordinate system of the reference medical image.

In some embodiments, system 20 comprises a video display 52 that shows an image 55 taken by camera 50. In the shown image, a distal end of treating probe 39 can be seen engaging brain tissue.

In some embodiments, processor 34 is configured to receive, via an interface (not shown), one or more anatomical images, such as reference MRI images depicting two-dimensional (2D) slices of head 41. Processor 34 is configured to select one or more slices from the MRI images, perform registration with a real-time camera image, such as image 55, to produce a combined image, such as an image 35, and display the selected combined slice to physician 24 on user display 36. In the example of FIG. 1, combined image 35 depicts a sectional coronal view of anterior brain tissue of patient 22.

Console 33 further comprises input devices, such as a keyboard and a mouse, for controlling the operation of the console, and a user display 36, which is configured to display the data (e.g., images) received from processor 34 and/or to display inputs inserted by a user using the input devices (e.g., by physician 24).

FIG. 1 shows only elements related to the disclosed techniques for the sake of simplicity and clarity. System 20 typically comprises additional or alternative modules and elements that are not directly related to the disclosed techniques, and thus are intentionally omitted from FIG. 1 and from the corresponding description.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components. In particular, processor 34 runs a dedicated algorithm as disclosed herein, including in FIG. 3, that enables processor 34 to perform the disclosed steps, as further described below.

Trocar with Modular Trocar Obturator Head

Figure 2:
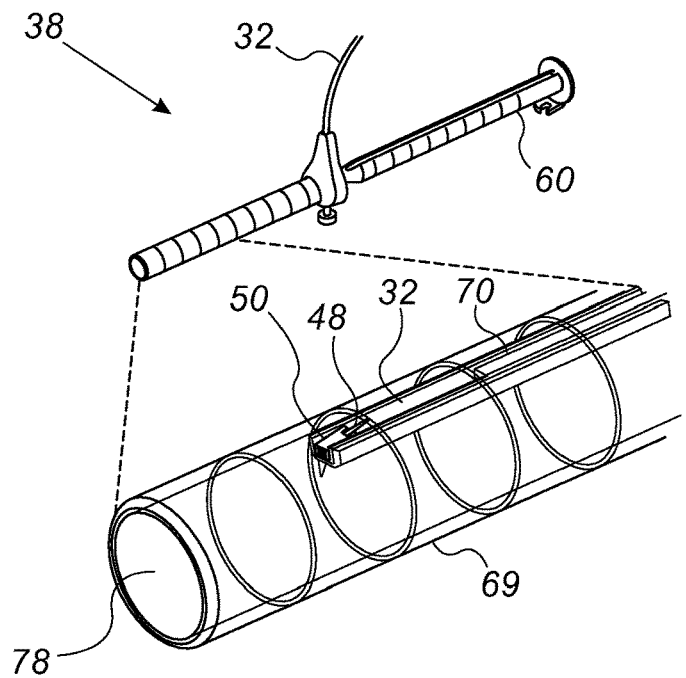
FIG. 2 is a schematic, pictorial illustration of the trocar applied in the brain procedure of FIG. 1, in accordance with an embodiment of the present invention.

FIG. 2 is a schematic, pictorial illustration of trocar 38 applied in the brain procedure of FIG. 1, in accordance with an embodiment of the present invention. Trocar 38 comprises a cannula 69 and an obturator 60. As seen, trocar 38 comprises a channel 70 inside cannula 69, channel 70 having a distal edge on which camera 50 and position sensor 48 are mounted. Channel 70 further provides a track for routing cable 32.

In an embodiment, camera 50 is tilted relative to the longitudinal axis of trocar 38, so as to have a central distal viewing direction pointing at a center of a distal opening 78 of cannula 69. At the same time, sensor 48 is mounted such that the sensor does not obstruct the field of view of camera 50.

The configuration of trocar 38 in FIG. 2 is depicted by way of example for the sake of conceptual clarity. In other embodiments, additional elements may be included, such as additional ports in trocar 38 to insert medical tools to the target brain location.

Figure 3:
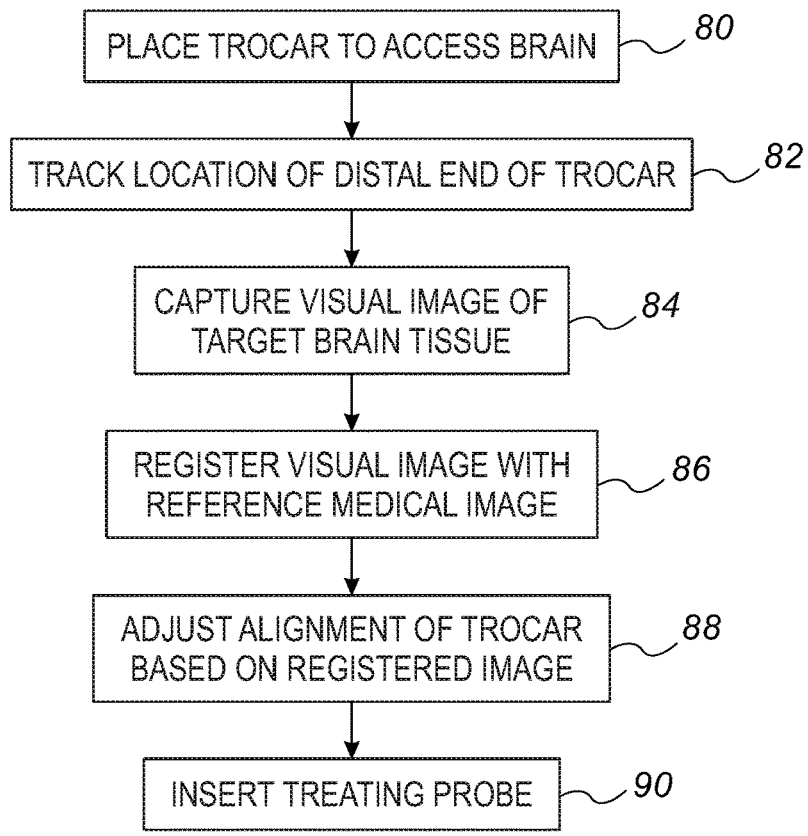
FIG. 3 is a flow chart that schematically illustrates a method and algorithm for registering a visual image from the camera of the trocar of FIG. 2 with a reference medical image, in accordance with an embodiment of the present invention.

FIG. 3 is a flow chart that schematically illustrates a method and algorithm for registering a visual image from camera 50 of trocar 38 of FIG. 2 with a reference medical image, in accordance with an embodiment of the present invention. The process begins when physician 24 places trocar 38 to access the brain, at a trocar placement step 80.

Next, physician 24 operates system 20 to magnetically track a location in the brain of a distal end of trocar 38 using signals from sensor 48, at a trocar position tracking step 82. Next, in an image capturing step 84, physician 24 captures an image by camera 50, to register with a reference medical image.

At an image registration step 86, based on the tracked position of trocar's 38 distal end (using sensor 48), processor 34 registers the captured image (by camera 50) with a respective reference medical image stored in memory 49, such as from an MRI scan, to produce combined image 35. In an embodiment, processor 34 is further configured to correct the reference medical images based on the registered images, for example, if the treatment removes brain tissue. In another embodiment, the processor is further configured to alert a user to a detected discrepancy between the visual image and the reference image due to, for example, a larger tumor size detected by camera 50 because of tumor growth since the reference image was taken.

Next, at a trocar adjustment step 88, using combined image 35, physician 24 adjusts an alignment of trocar 38, e.g., to best allow best access to target brain tissue, such as an infected tissue. Physician 24 then inserts a treating probe 39, at a probe insertion step 90, to treat target tissue under visual guidance provided by camera 50.

The example flow chart shown in FIG. 3 is chosen purely for the sake of conceptual clarity. In alternative embodiments physician 24 may perform additional steps, such as employing additional monitoring steps (e.g., fluoroscopy) to verify the successful outcome of the procedure, and/or apply irrigation to clear view for camera 50.

Navigated Trocar with Internal Camera and Modular Obturator Head

Figure 4:
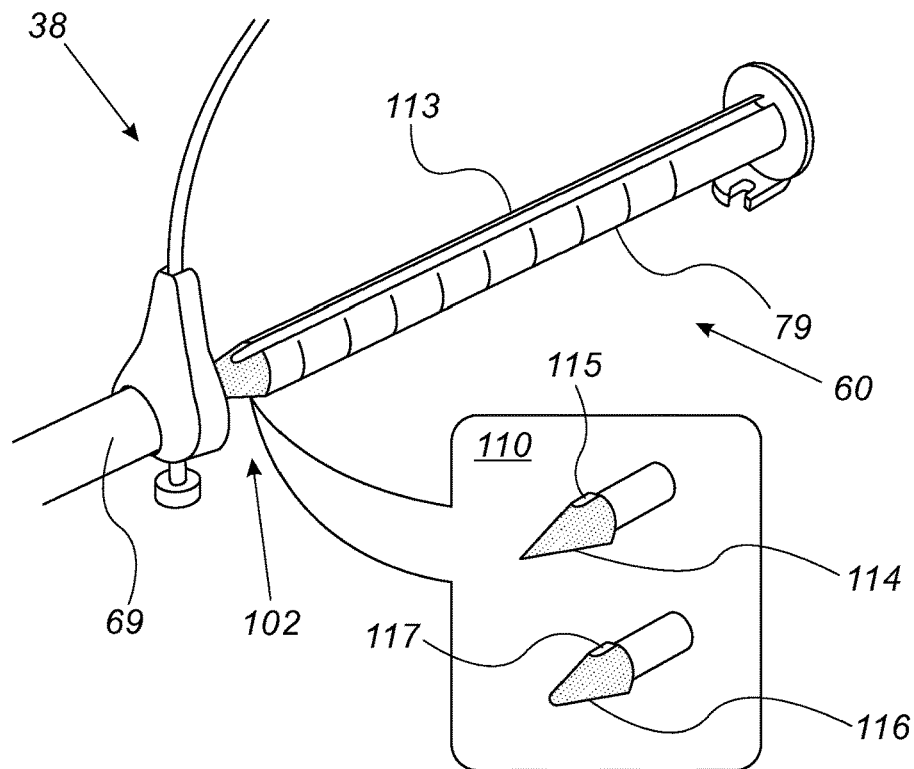
FIG. 4 is a schematic, pictorial illustration of the trocar applied in the brain procedure of FIG. 1, in accordance with another embodiment of the present invention.

FIG. 4 is a schematic, pictorial illustration of trocar 38 applied in the brain procedure of FIG. 1, in accordance with another embodiment of the present invention. Trocar 38 includes cannula 69 and an obturator 60. As seen, trocar 38 includes a modular obturator 60 which is comprises an obturator body 79 configured to be inserted into cannula 69 of trocar 38. An obturator head 102 of obturator 60 is configured to penetrate the body and create access for the probe.

Obturator body 79 of modular obturator 60 is constructed such that different obturator heads can be interchangeably fitted to obturator body 79, few heads seen by way of example in inset 110, which can be used during an invasive medical procedure. In inset 110, an obturator head 114 has a sharp tip, and is typically used to penetrate muscle or bone. An obturator head 116, on the other hand, has a smooth tip, and may be used to penetrate brain tissue.

As further seen, obturator body 79 and interchangeable obturator heads 114 and 116 are designed with depressions 113, 115, and 117 respectively, such that they could be readily fit (e.g., inserted into) cannula 69, where depressions 113, 115, and 117 match a profile of channel 70 (seen in FIG. 2).

The configuration of trocar 38 in FIG. 4 is depicted by way of example for the sake of conceptual clarity. In other embodiments, additional elements may be included, such as additional types of interchangeable obturator heads.

Figure 5:
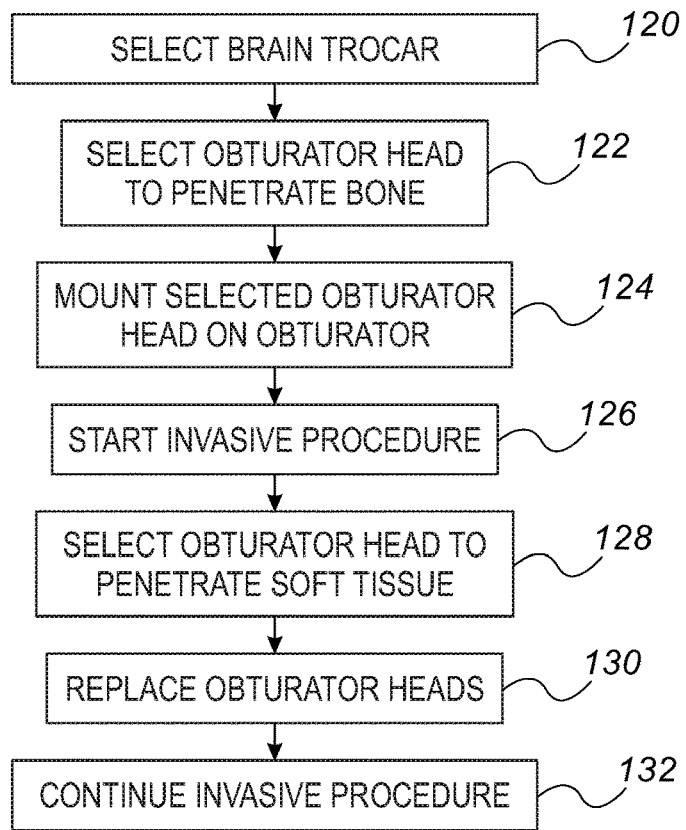
FIG. 5 is a flow chart that schematically illustrates a method of using the trocar of FIG. 4 with interchangeable obturator heads, in accordance with an embodiment of the present invention.

FIG. 5 is a flow chart that schematically illustrates a method of using the trocar of FIG. 4 with interchangeable obturator heads (114, 116), in accordance with an embodiment of the present invention. The process begins with physician selecting a brain trocar 38 to access the brain, at a trocar selection step 120.

Next, physician 24 selects an interchangeable obturator head capable of penetrating bone, such as interchangeable obturator head 114, at an obturator head selection step 122. The physician mounts selected obturator head 114 on obturator 60, in obturator preparation step 124.

At a treatment step 126, physician 24 uses the assembled obturator to start an invasive procedure, such as using the obturator to penetrate skull bone.

To continue obturator placement in the brain, physician 24 selects, at an obturator head selection step 128, obturator head 116, which is configured to enter the brain tissue. At an obturator head replacement step 130 physician 24 replaces obturator head 114 with obturator head 116. Finally, at a treatment step 132, physician 24 uses the re-assembled obturator to continue the invasive procedure, by advancing the obturator in brain tissue.

The example flow chart shown in FIG. 5 is chosen purely for the sake of conceptual clarity. In typical embodiments physician 24 will perform additional steps, such as advancing cannula 69, while tracking a position of the cannula.

Although the embodiments described herein mainly address brain procedures, the methods and systems described herein can also be used in other applications that require guiding a medical device in other organs, such as located in the abdomen or the chest.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A trocar for insertion into a patient, the trocar comprising:
   (a) a cannula having a longitudinal axis and a channel inside the cannula, the channel being oriented parallel to the longitudinal axis;
   (b) an obturator body, configured to be inserted into the cannula, the obturator body including a depression configured to conform with the channel inside the cannula when the obturator is inserted into the cannula; and
   (c) two or more interchangeable obturator heads, each configured to be detachably fitted at a distal end of the obturator body, wherein each obturator head of the two or more interchangeable obturator heads comprises a head depression to conform with the channel inside the cannula when the obturator is inserted into the cannula.

2. The trocar according to claim 1, wherein the obturator heads have different respective geometries for penetrating different respective tissue types.

3. The trocar according to claim 1, wherein the interchangeable obturator heads are configured for use in an invasive brain procedure.

4. The trocar according to claim 1, and comprising:
   (a) a camera, which is disposed at a distal end of the channel and is configured to provide images in a direction of a distal opening of the cannula; and
   (b) a position sensor, which is disposed at a distal end of the channel without obstructing a field of view of the camera, and is configured to generate signals indicative of a position of the distal end.

5. The trocar according to claim 4, wherein the camera is tilted to have a center viewing direction of the camera point at a center of the distal opening of the cannula.

6. The trocar according to claim 4, wherein the position sensor is a magnetic position sensor.

7. A method, comprising:
   (a) selecting an obturator head from among two or more interchangeable obturator heads;
   (b) detachably fitting the selected obturator head at a distal end of an obturator body, to form an obturator;
   (c) assembling a trocar by fitting the obturator in a cannula;
   (d) inserting the trocar into a brain of a patient, so as to perform a medical procedure on the patient;
   (e) acquiring images in a direction of a distal opening of the cannula, by a camera disposed at a distal end of the cannula;
   (f) using a position sensor disposed at a distal end of a channel of the cannula, without obstructing a field of view of the camera, generating signals indicative of a position of the distal end in the brain; and
   (g) using the generated signals, estimating the position of the distal end of the trocar in the brain.

8. The method according to claim 7, wherein the obturator heads have different respective geometries for penetrating different respective tissue types.

9. The method according to claim 7, wherein the medical procedure comprises an invasive brain procedure.

10. The method according to claim 7, and comprising:
    (a) based on the estimated position, registering an image acquired by the camera with a reference medical image; and
    (b) presenting the image acquired by the camera and the reference medical image, registered with one another, to a user.

11. The method according to claim 7, wherein the position sensor is a magnetic position sensor.

12. The trocar according to claim 2, wherein an obturator head of the two or more interchangeable obturator heads comprises a sharp tip configured to penetrate bone.

13. The trocar according to claim 2, wherein an obturator head of the two or more interchangeable obturator heads comprises a sharp tip configured to penetrate muscle.

14. The trocar according to claim 2, wherein an obturator head of the two or more interchangeable obturator heads comprises a smooth tip configured to penetrate brain tissue.

15. The trocar according to claim 1, wherein the obturator body is configured to be slidable inside the cannula and along the longitudinal axis.

16. A trocar for insertion into a patient, the trocar comprising:
    (a) a cannula having a central longitudinal axis and a channel inside the cannula, the channel being oriented parallel to the longitudinal axis and laterally offset from the central longitudinal axis;
    (b) an obturator body, configured to be inserted into the cannula; and
    (c) a detachable obturator head configured to be detachably fitted at a distal end of the obturator body, the obturator head including a depression configured to conform with the channel inside the cannula when the obturator is being inserted into the cannula.

17. The trocar according to claim 16, and comprising a camera, which is disposed at a distal end of a channel of the cannula and is configured to provide images in a direction of a distal opening of the cannula.

* * * * *